United States Patent
Najanguaq Søvsø Andreasen Struijk

(10) Patent No.: US 8,018,320 B2
(45) Date of Patent: Sep. 13, 2011

(54) TONGUE BASED CONTROL METHOD AND SYSTEM FOR PERFORMING THE METHOD

(75) Inventor: Lotte Najanguaq Søvsø Andreasen Struijk, Terndrup (DK)

(73) Assignee: TKS A/S, Aalborgost (DK)

( * ) Notice: Subject to any disclaimer, the term of this patent is extended or adjusted under 35 U.S.C. 154(b) by 998 days.

(21) Appl. No.: 11/887,950

(22) PCT Filed: Apr. 7, 2006

(86) PCT No.: PCT/DK2006/000201
§ 371 (c)(1),
(2), (4) Date: Oct. 5, 2007

(87) PCT Pub. No.: WO2006/105797
PCT Pub. Date: Oct. 12, 2006

(65) Prior Publication Data
US 2009/0051564 A1    Feb. 26, 2009

(30) Foreign Application Priority Data
Apr. 7, 2005    (DK) .................................. 2005 00491

(51) Int. Cl.
*G09B 21/00*    (2006.01)
(52) U.S. Cl. ............... 340/4.11; 340/539.12; 340/539.22
(58) Field of Classification Search ............. 340/825.19; 702/116; 600/590; 178/18.03, 18.07; 323/355; 324/207.11
See application file for complete search history.

(56) References Cited

U.S. PATENT DOCUMENTS

| | | | |
|---|---|---|---|
| 3,596,173 A * | 7/1971 | Cohen | 323/355 |
| 4,054,746 A | 10/1977 | Kamm | |
| 4,334,542 A * | 6/1982 | Takinishi et al. | 600/383 |
| 5,212,476 A | 5/1993 | Maloney | |
| 5,453,687 A | 9/1995 | Zierdt et al. | |
| 5,460,186 A | 10/1995 | Buchhold | |
| 5,689,246 A | 11/1997 | Dordick et al. | |
| 5,977,752 A * | 11/1999 | Schulz | 322/3 |
| 6,598,006 B1 * | 7/2003 | Honda et al. | 702/116 |
| 2010/0007512 A1 * | 1/2010 | Ghovanloo et al. | 340/825.19 |

FOREIGN PATENT DOCUMENTS

| | | |
|---|---|---|
| EP | 0 734 704 B1 | 11/2001 |
| WO | 93/07726 A1 | 4/1993 |
| WO | 2004/084775 A1 | 10/2004 |

* cited by examiner

*Primary Examiner* — Benjamin C Lee
*Assistant Examiner* — Peter Mehravari
(74) *Attorney, Agent, or Firm* — The Nath Law Group; Jerald L. Meyer; Jiaxiao Zhang

(57) ABSTRACT

With a method and a System for tongue based control of computers and/or aids, particularly for severely disabled persons it is the intention to ease the communication capabilities of severely disabled persons and their control of their aids, where the costs of producing the system are low, thereby avoiding the drawbacks of the prior art. This goal is achieved with a method and a system, where the method comprises that the interaction between the arrangement and the tongue is based on induction, whereby the arrangement is equipped with at least one coil being able to interact with at least one piece of a magnetic responsible material fixed to the tongue, and that the signals transmitted to the device further comprise the position of the coil in the arrangement and/or the position of the magnetic responsible material fixed to the tongue, and the system comprises that the arrangement is equipped with at least one coil being able to interact with at least one piece of a magnetic responsible material fixed to the tongue, and that the signals transmitted to the device further comprise the position of the coil in the arrangement and/or the position of the magnetic responsible material fixed to the tongue.

8 Claims, 5 Drawing Sheets

RESULTS

TONGUE BASED CONTROL METHOD AND SYSTEM FOR PERFORMING THE METHOD

TECHNICAL FIELD

Figure 1:
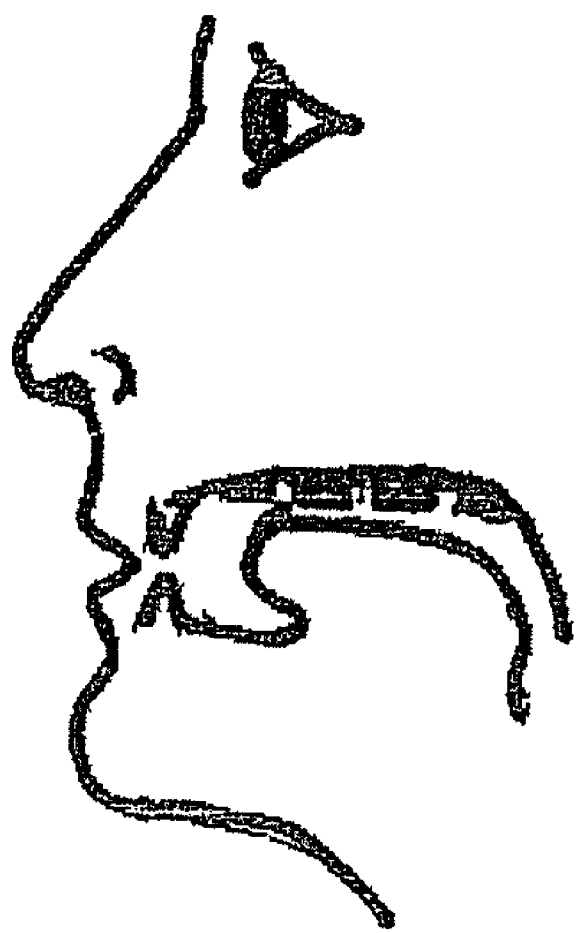

The present invention relates to a method for tongue based control of computers and/or aids, particularly for severely disabled persons, comprising:

Activation of a mouth cavity arrangement, preferably a palatal arrangement interacting with the tongue;

processing of signals emanating from the interaction between the arrangement and the tongue, and communicating the processed signals to a device.

The invention further relates to a system for tongue based control of computers and/or aids, particularly for severely disabled persons, comprising:

a mouth cavity arrangement, preferably a palatal arrangement, being able to interact with the tongue;

at least one signal processor for the processing of the signals emanating from the interaction between the arrangement and the tongue, and a communicator unit for transmitting the processed signals to the device.

BACKGROUND ART

People with movement disabilities because of spinal cord injury, brain injury or other impairments of the motor system are greatly affected in their everyday life, in many cases to the extent that everyday life is impossible without continuous help. In Denmark there are more than 30,000 wheelchair users, and in the U.S. there are 200,000 people with spinal cord injuries. Any increase of self-supportiveness, maybe even to the ability of possessing a job, is crucial to improve the quality of life for these disabled individuals.

With the modern Internet and communication technology, jobs, sociability and even health care is no longer linked to the physical presence of the persons involved, but the internet has become a virtual world in which only the computer access limits the individual contribution. Here severely paralysed persons, who have lost even the ability to speak and for whom the only way of real communication is through a computer, could even possess jobs, and thereby highly improve their quality of life, as long as they have an efficient computer control. With the increased computerisation of everyday equipment, such as automatic doors, kitchen hardware, telephones, TVs, several everyday tasks can be automated. While this automation is convenient for most of us, it is potentially invaluable for increasing independence and quality of life for disabled persons. An effective control method to access these things can significantly improve the quality of life for millions of disabled all over the world.

Currently, the most successful control methods within communication are eye control devices (Gips J, DiMattia P, Curran F X and Olivieri P, "*Using EagleEyes—an Electrodes Based Device for Controlling the Computer with Your Eyes*", in "*Interdisciplinary Aspects on Computers Helping People with Special needs*" J. Klaus, e. Auff, W. Kremser, W. Zagler (eds.). R Oldenbourg, Vienna, 1996, LC Technologies, Inc. Eyegaze Systems Eyetracking 9455 Silver King Court Fairfax, Va. 22031), head control devices, voice recognition and the tongue control device (Patent: WO9307726, New Abilities Systems Inc., 1993). Still there are a number of problems related to the effectiveness of the use of these methods. The use of the eye for control demands high concentration and often results in headaches, one. explanation of the problems with this method is the fact that the eye is a sensor or an input device, and that makes it difficult for the brain to learn the control in which the eye is an output device. Problems are also related to determining whether a point of interest is found by the user or the user is simply gazing, the latter leading to false detections. Voice recognition is quite a fast way to effectuate a command, but may be sensitive to interference. Further, it is limited to be used by the disabled with intact language, and it has not been developed for all languages. The head control systems often demands high concentration and the requirement of exact control of the head movements often results in neck pain.

The tongue control methods are favourable since they are practically invisible and manageable for people with even severe disabilities. A comparative study, comparing a tongue control method to a head control system and a rather simple mouth stick, resulted in all four quadriplegic test persons preferring the tongue based control system, even though it was not the fastest system (C. Lau and S. O'Leary, "*Comparison of Computer Interface Devices for Persons with Severe Physical Disabilities*", The American Journal of Occupational Therapy, vol. 47, pp. 1022-1030, 1993). Current tongue control systems are mainly based on pressure sensitive buttons placed in the mouth cavity over the tongue (Patent: WO9307726, New Abilities Systems Inc., 1993). The use of pressure sensitive sensors does not seem optimal, since normal speech and swallowing generates tongue-palatal pressures in the range of 20-60% of maximal achievable pressure (Müller, E, at al. "*Perioral tissue mechanics during speech production*". In J. Eisenfeld & C. DeLisi (Eds.) "*Mathematics and computers in biomedical application*" Elsevier Science publishers B.V., 1984", Hayashi R, Tsuga K, Hosokawa R, et al., "*A novel handy probe for tongue pressure measurement*" International Journal Of Prosthodontics 15(4): 385-388 JULY-AUGUST 2002), which poses demands on the detection threshold and therefore may increase the risk of fatigue. Further the use of pressure-based sensors strongly limits the maximal number of sensors that can be placed in the oral cavity since the pressure increase the tongue-palatal contact area. Having only 9 control buttons the commercially available tongue touch keypad from New Abilities Systems (Patent: WO9307726, New Abilities Systems Inc., 1993) far from utilizes the high selectivity in the movement of the tongue, which readily can pick out every single of our 32 teeth. This selectivity is in theory sufficient to select the alphabet directly on 26 buttons, although a different sensor type will have to be developed. Such a direct letter selection would bring the typing ability of a quadriplegic on the level of an intact person using one finger. This would make communication much more effective and attractive. Moreover, a variety of electric aids, including wheelchairs and neural prostheses, would be controllable with a wide range of commands from the same interface. Therefore, this work describes a new sensor and method to facilitate tongue-activated commands.

It is the object of the invention to provide a method and a system for easing the communications capabilities of severely disabled persons and their control of their aids, where the costs of producing the system are low, thereby avoiding the drawbacks of the above mentioned prior art.

DISCLOSURE OF INVENTION

This aim is achieved by means of the method and the system as mentioned in the claims 1 and 4. Further improvements are presented in the dependent claims.

Methods:

Theory.

The detection method used in this work is based on Faraday's law of induction for a coil, and uses variable inductance techniques. The idea is to change the inductance of an air-cored induction coil, by moving a ferromagnetic material, attached to the tongue, into the core of the coils (FIG. 1): From Faradays law the voltage drop across an inductance can be found as:

$$\epsilon = -L di/dt = \mu_0 \cdot \mu_r \cdot N^2 \cdot A/l \cdot di/dt$$

Where
$L = \mu_0 \cdot \mu_r \cdot N^2 \cdot A/l$
L=inductance
$\mu_0$=vacuum permeability
$\mu_r$=relative magnetic permeability of the core material
N=number of turns
l=is the average length of the magnetic flux path When only air is present as the core of the inductance, $\mu_r=1$. As the ferromagnetic material is placed in the coil, the core becomes a combination of air and ferromagnetic material and $\mu_r$ changes according to the magnetic permeability of the ferromagnetic material.

By applying a sine wave current, i, of constant peak-peak amplitude, a constant amplitude voltage drop $\epsilon$ is obtained across the coil L. Introduction of the ferromagnetic material into the air gap of the coil, results in an increase of $\epsilon$, which stays increased, until the material is removed. This will be utilized for activation of a command in the inductive tongue control system. The method resembles the know techniques used for displacement sensors (Göpel, W, Hesse, J. Zemel, J N "*Magnetic sensors*", in Sensors, a comprehensive Survey" Volume 5, VCH, Verlagsgesellschaft mbH, D-6940 Weinheim, 1989).

BRIEF DESCRIPTION OF THE DRAWING(S)

Figure 2:
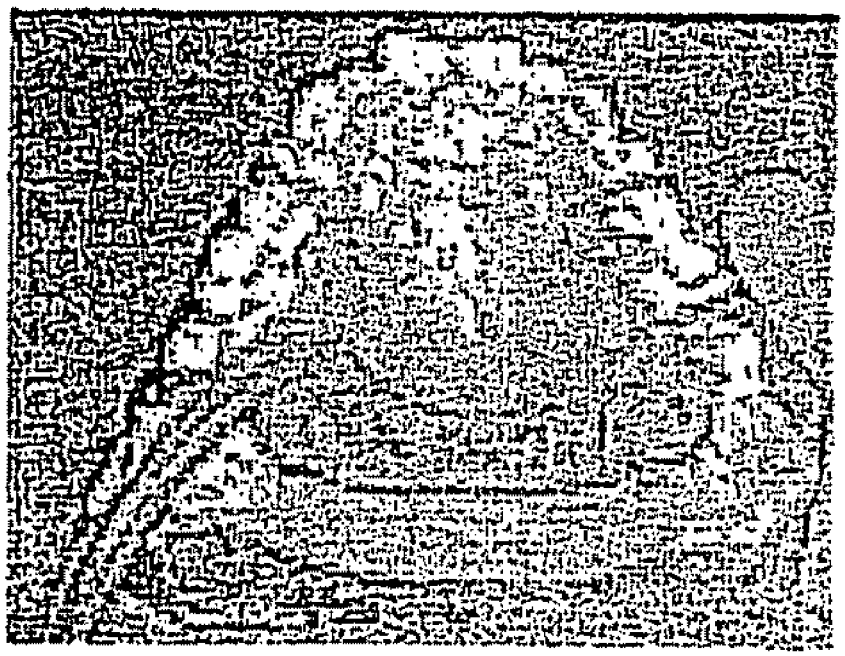
Figure 3:
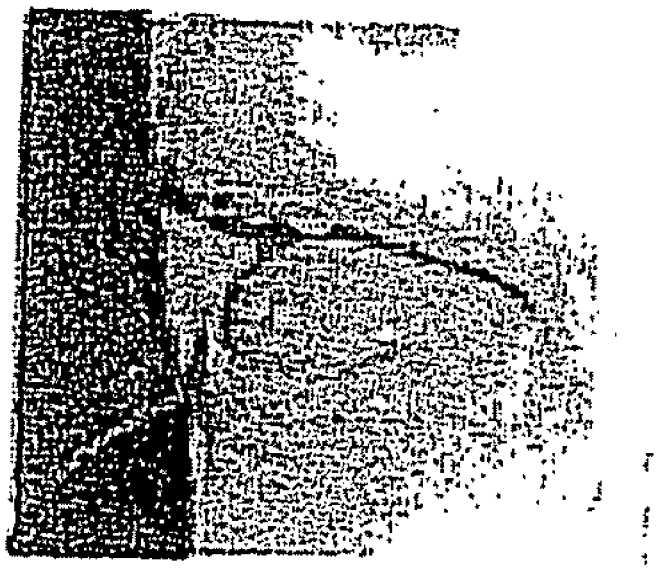
Figure 4:
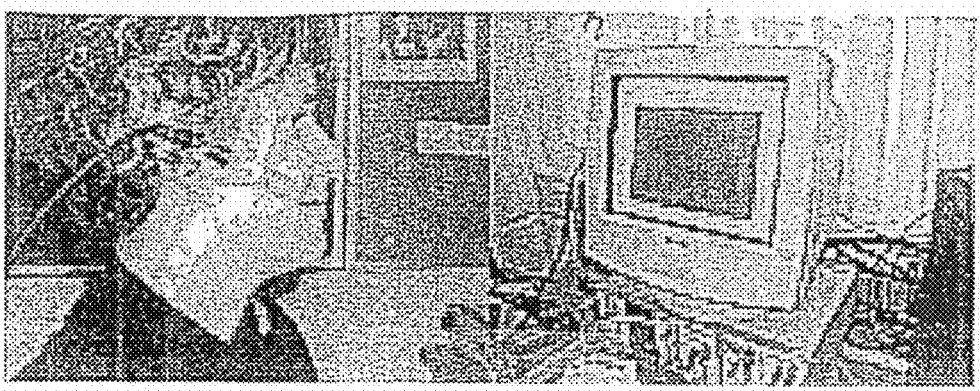
Figure 5:
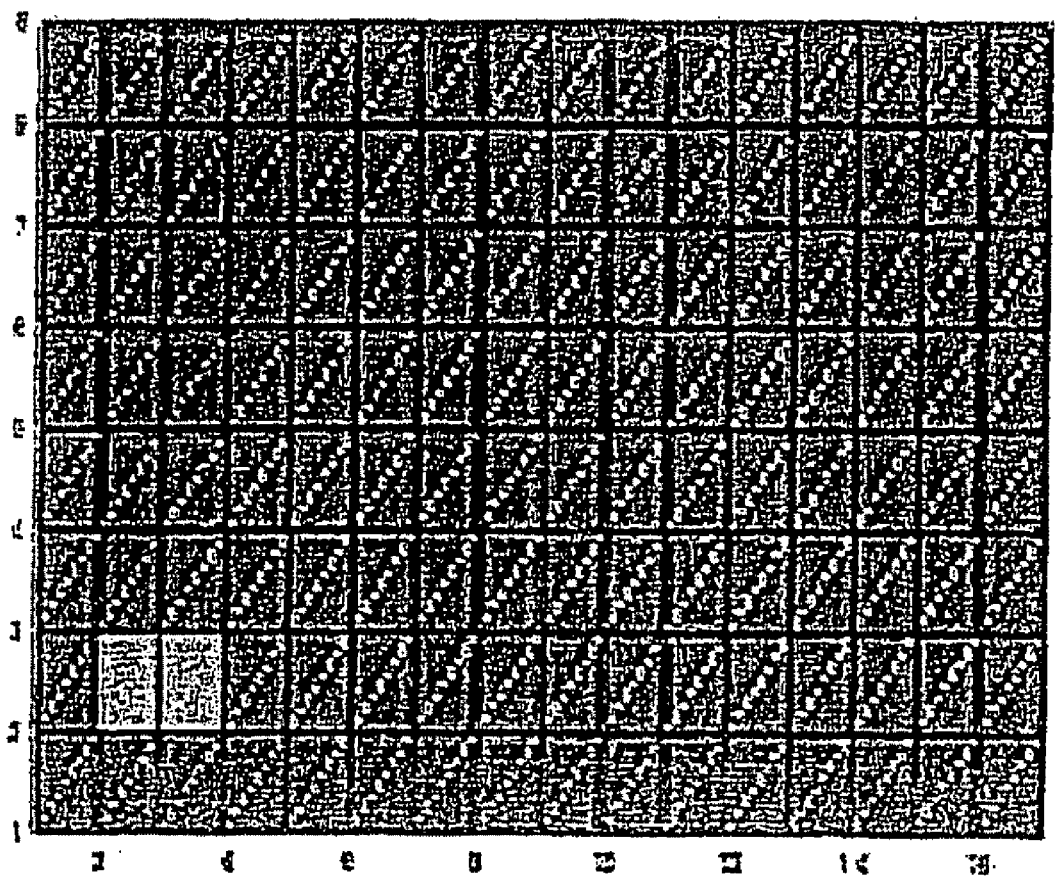

Below, the invention will be explained in detail with reference to an embodiment shown in the enclosed drawing, in which:

FIG. 1 shows a schematic saggital sectional view of the user part of the inductive tongue control system according to the invention, FIG. 2 the palatal arrangement according to the present invention with inductive coils arranged as an example in a dental prosthesis (denture), FIG. 3 an activation unit made of a magnetic responsible material mounted on the tongue of a person, FIG. 4 an example of an experimental set-up with a user connected to external units by wire, and FIG. 5 an example of a visual feed-back display during activation of a sensor in the palatal arrangement.

BEST MODE(S) FOR CARRYING OUT THE INVENTION

Design of the Inductive Sensor.
The sensor consists of two parts.
1. A coil that will be placed in the oral cavity using a palatal arrangement.
2. An activation unit made of a magnetic material that will be placed on the tongue.
The Inductor.

4 inductors were produced having a different number of turns N, to be able to distinguish in-between, which coil that was activated using thresholding. The inner diameter of the coils was 4 mm. The used wire was a cobber wire insulated with polyesterimide, and the conducting part of the wire had a diameter of 0.1 mm (Dahréntrad).

The windings of the coils were stabilized using Paladur® powder/liquid cold-cure dental acrylic, based on methyl-methacrylate. After winding the coil, it was dipped into the acrylic to achieve additional electrical insulation.

The Activation Unit.

The activation unit consists of a cylindrical piece of stainless steel of the type SUS447J1, which has been approved by the Japan Ministry of health and Welfare for magnetic attachment of dentures (Okuno, O, Ishikawa, S, Iimuro, F T, Kinouchi, Y, Yamada, H, Nakano, T, Hamanaka, H. Ishihata, N, Mizutani, H and Ai, M, "*Development of Sealed Cup Yoko Type Dent al Magnetic Attachment*", Dental Materials Journal, 10 (2), pp. 172-184, 1991). The diameter of the cylinder was 3.2 mm and the height was 2 mm. The steel had a maximum magnetic permeability $\mu_r$ of 2000-6500.

Mounting of Sensors on at the Palatal Arrangement.

The inductors were placed on a palatal plate resembling the ones used in dentures, cf. FIG. 2. Holes were drilled in the palatal plate for the coils and methylmethacrylate was used to fix and insulate the coils. The wires from the coils were additionally insulated electrically using silicone (MED-1137 from Nusil), applied to the acrylic with a silicone bonder (SP-120 from Nusil). A silicone tube was fixed to the dental palate with the bonder and carried the wires out of the mouth, cf. FIG. 2.

Experimental Setup.

The Inductive Tongue Control System was tested in a 37 year old, healthy female.

The activation unit was glued to the tongue using n-butyl-2-cyanoacrylate tissue glue (Histoacryl®), cf. FIG. 3.

The palatal plate with the inductors was placed at the hard palate, and kept in place by the clamps of the plate. The inductors were connected in serial, and a 30 kHz sine wave current with a 0.5 mA amplitude was applied to the inductors from a galvanically isolated current source. The subject activated the sensors, one at the time, by positioning the tongue in a manner that placed the activating unit in the centre of the different coils in arbitrary order.

Signal Processing.

The measured signal was amplified 700 times and rectified to obtain an envelope of the signal. The signal was sampled and processed using the Matlab DAQ toolbox. Thresholding was applied to the measured signal in order to determine which sensor had been activated, and that information was fed into custom-made Matlab program providing a real-time visual display of a grid, resembling the palatal arrangement with the sensors, FIG. 4. From this visual display, the subject could see which sensor had been activated.

Results.

The measured voltage was in the range of 5.7 mV, which increased to 6 m V during activation of a coil with 100 turns.

The total size of the designed inductors, given as the outer diameter was 5-6 mm, indicating the possibility of having more than 25 sensors in the palatal arrangement of future Inductive Tongue Control Systems. The subject could readily activate desired sensors. Activation of the sensors is not conditioned the actual placement of the activation unit inside the coil, but it is sufficient to place the activation unit at the coil.

As expected an activated sensor stayed activated until the activation unit was removed from, that coil. The time that the activation unit stayed fixed to the tongue was in the order of minutes and therefore other methods for experimental fixation of the activation unit may be considered in future work.

Discussion.

For a control system to be truly successful it has, in reality, to be a help for the user. This may imply that the system:
Can be used/worn all day and night
Is easy to use and induces a low degree of fatigue
Is cosmetically acceptable in and outside the home of the user—preferably invisible.

Can be used to control a wide range of equipment, e.g. computers, wheelchairs, toys and prosthesis.

Provides an efficient and quick activation of the desired function.

All these requirements can be met with this new system, facilitating partly implantable inductive sensors.

The small size of the sensor-coils opens up for the possibility of having the whole alphabet, as separate "buttons" on the palatal arrangement, which may lead to a substantial increase in e.g. the rate of writing for quadriplegics. Further, the use of multiple activation units in or on the tongue allows for multiple activation of sensors, where a side-lisp activation could be used to activate a "shift key", an "Enter key", and/or a "control key" function during activation of other sensors in the palatal arrangement. Future studies in tongue selectivity may reveal more information about feasibility of these possibilities.

The recorded signals from the sensors were of low amplitude, but if needed, there are several possibilities to increase the amplitude of the sensor output, e.g. by an increase in frequency or of the amplitude of the applied current, which were kept low in this study. Sensing and transmitting asynchronously could prevent possible interference from a future wireless transmission of the sensor output. This, of course, would necessitate a storage system in the palatal arrangement.

In the present embodiment the coils were connected in serial, and the measured signal was related to all the inductances and the implicit resistance of the coil wire. A current with fixed frequency and fixed amplitude was applied, and the number of turns of each coil was the only parameter that made it possible to determinate which coil was activated. This is a very simple set-up and an advantage is that only two leads are needed to measure from and supply several sensors. Many other configurations could be considered, and e.g. thresholding could be avoided using the coils as frequency detectors instead. Also, the coils could be connected in parallel to a signal generator. Such generator could be placed in the palatal arrangement.

One new feature of the Inductive Tongue Control System as compared to traditional computer control systems is that it is partly implantable, due to the activation unit. Future systems may incorporate fixation of the activation unit by piercing or by implantation right under the tongue mucosa e.g. through injection. Thus the degree of invasiveness is rather low.

The advantage of the partly implantable sensors as compared to the traditionally pressure based tongue interfaces is besides the possibility of having a high number of sensors/buttons, that practically no force is needed for activation and that the activation therefore is faster and less fatiguing. Further, the system is not affected by the tongue palatal-pressures related to normal eating and speaking.

Naturally, modifications of the invention are possible within the scope of the present invention. For example, incorporating wireless control in the Induction Tongue Control System, e.g. the "Blue Tooth" protocol, and developing command strategies to control a wide range of devices.

The invention claimed is:

1. A method for tongue based control of computers and/or aids, particularly for severely disabled persons, comprising:
   activating a palatal mouth cavity arrangement, interacting with the tongue;
   processing signals emanating from the interaction between the arrangement and the tongue; and
   communicating the processed signals to a device, wherein
   the interaction between the arrangement and the tongue is based on induction, whereby the arrangement is equipped with at least one coil being able to interact with at least one piece of a ferromagnetic material fixed to the tongue, and
   the signals transmitted to the device further comprise the position of the coil in the arrangement and/or the position of the ferromagnetic material fixed to the tongue.

2. The method according to claim 1, wherein
   the signals comprise a carrier current of constant peak-to-peak-amplitude being moderated by the coils in the arrangement when interacting with the magnetic responsible material fixed to the tongue.

3. The method according to claim 1, wherein
   the device performs a processing of the signals coming from the arrangement so as to control the computers and/or aids.

4. A system for tongue based control of computers and/or aids, particularly for severely disabled persons, comprising:
   a palatal mouth cavity arrangement, being able to interact with the tongue;
   at least one signal processor for the processing of the signals emanating from the interaction between the arrangement and the tongue; and
   a communicator unit for transmitting the processed signals to a device, wherein
   the interaction between the arrangement and the tongue is based on induction, whereby the arrangement comprises at least one coil being able to interact with at least one piece of a ferromagnetic material fixed to the tongue, and
   the signals transmitted to the device further comprise the position of the coil in the arrangement and/or the position of the ferromagnetic material fixed to the tongue.

5. The system for tongue based control of computers and/or aids according to claim 4, wherein
   the communicator unit is a part of the arrangement and further comprises a decoder for the origin of the signals coming from the at least one coil,
   each coil comprises an individual number of windings, and the arrangement includes a battery compartment.

6. The system for tongue based control of computers and aids according to claim 4, wherein
   the communicator unit further comprises a transmitter for the communication to the computers and/or aids.

7. The system for tongue based control of computers and aids according to claim 6, wherein
   the transmitter for the communicator unit to the computers and/or aids is a wireless transmitter, which is configured to the "Blue Tooth"-protocol.

8. The system for tongue based control of computers and aids according to claim 7, wherein
   at least two coils are connected in series.

* * * * *